United States Patent
Chan et al.

(10) Patent No.: US 7,060,111 B2
(45) Date of Patent: *Jun. 13, 2006

(54) METHOD FOR PROVIDING MORE VIBRANT, NATURAL AND LONG-LASTING COLOR TO HAIR

(75) Inventors: Alexander C. Chan, Cranbury, NJ (US); Padmaja Prem, Saddle Brook, NJ (US); John Brian Bartolone, Bridgeport, CT (US)

(73) Assignee: Unilever Home & Personal Care USA, division of Conopco, Inc., Chicago, IL (US)

( * ) Notice: Subject to any disclaimer, the term of this patent is extended or adjusted under 35 U.S.C. 154(b) by 284 days.

This patent is subject to a terminal disclaimer.

(21) Appl. No.: 10/613,792

(22) Filed: Jul. 3, 2003

(65) Prior Publication Data
US 2005/0000035 A1    Jan. 6, 2005

(51) Int. Cl.
*A61K 7/13*    (2006.01)
(52) U.S. Cl. .................. 8/405; 8/406; 8/408; 8/410; 8/411; 8/412; 8/435; 132/208; 424/70.1
(58) Field of Classification Search ............ 8/405, 8/406, 408, 410, 411, 412, 435; 132/208; 424/70.1
See application file for complete search history.

(56) References Cited

U.S. PATENT DOCUMENTS

| | | | |
|---|---|---|---|
| 2,934,396 A | 4/1960 | Charle et al. ................ 8/11 |
| 3,194,734 A | 7/1965 | Seemuller et al. ........... 167/88 |
| 4,104,021 A | 8/1978 | Lapidus et al. ............... 8/10.2 |
| 4,268,264 A | 5/1981 | Grollier et al. ............... 8/410 |
| 4,314,810 A | 2/1982 | Fourcadier et al. .......... 8/410 |
| 4,370,142 A | 1/1983 | Bugaut et al. ................ 8/407 |
| 4,425,132 A | 1/1984 | Grollier et al. ............... 8/405 |
| 4,566,875 A | 1/1986 | Grollier et al. ............... 8/406 |
| 4,804,385 A | 2/1989 | Grollier et al. ............... 8/423 |
| 4,888,027 A | 12/1989 | Grollier et al. ............... 8/423 |
| 5,173,085 A | 12/1992 | Brown et al. ................. 8/405 |
| 5,279,620 A | 1/1994 | Junino et al. ................ 8/409 |
| 5,525,123 A | 6/1996 | Lorenz et al. ................ 8/408 |
| 5,980,586 A | 11/1999 | Wenke et al. ................ 8/424 |
| 6,238,439 B1 | 5/2001 | Cotteret ....................... 8/409 |
| 6,540,791 B1 * | 4/2003 | Dias ............................. 8/405 |
| 2003/0154562 A1 * | 8/2003 | Sarojini et al. .............. 8/405 |

FOREIGN PATENT DOCUMENTS

| | | |
|---|---|---|
| EP | 0 146 350 A2 | 6/1985 |
| EP | 755 669 B1 | 1/1997 |
| GB | 2 205 329 A | 12/1988 |
| WO | 01/28508 A1 | 4/2001 |
| WO | 02/02062 A1 | 1/2002 |
| WO | 03/068177 A2 | 8/2003 |

OTHER PUBLICATIONS

Int'l. Search Report No. PCT/EP 2004/007060—dated Jul. 12, 2004—4 pp.
Co-pending U.S. Appl. No. 09/811,920; filed Mar. 19, 2001; Patel et al.; entitled "Method and Composition for the Gradual Permanent Coloring of Hair".
Co-pending U.S. Appl. No. 10/075,745; filed Feb. 14, 2002; Sarojini et al.; entitled "Two Step Permanent Coloring of Hair".
Co-pending application; Serial No. Not Assigned as of yet; filed Jul. 3, 2003; Chan et al.; entitled "Hair Dyeing Method Including an Aligning Step".

* cited by examiner

*Primary Examiner*—Eisa Elhilo
(74) *Attorney, Agent, or Firm*—Michael P. Aronson

(57) ABSTRACT

A sequential method for dyeing hair which comprises: contacting the hair with a substantially inactive dye precursor mixture containing at least one primary intermediate and an optional coupler having at least 50% of the molecules comprising these precursors are in their non-anionic form, for a period of time, followed by contacting the hair with a developer mixture capable of oxidizing the hair dye precursors to react and form hair color molecules.

14 Claims, No Drawings

METHOD FOR PROVIDING MORE VIBRANT, NATURAL AND LONG-LASTING COLOR TO HAIR

BACKGROUND OF INVENTION

The present invention relates to methods, and compositions for providing more vibrant, natural and long-lasting color to hair. The term vibrant as used herein refers to an optical quality in which the hair has a deep color yet appears bright as if light were emanating from within the hair fibers and not only being reflected at the surface. The method comprises two essential steps: contacting the hair for a period of time with a dye precursor mixture containing specific primary intermediates and couplers at defined pH conditions which control their state of ionization and developing the color by contacting the hair with a developer mixture. The invention also relates to kits providing the means to accomplish these steps.

Permanent hair colorants commonly come in two parts: a dye solution and a developer solution. In a conventional permanent hair coloring treatment, the dye solution and the developer solution are mixed and then immediately applied to the hair. After a time interval of about 25 to about 45 minutes, the hair is rinsed with water, treated with a post treatment conditioner, and then rinsed again with water.

The application of the dye solution and the developer solution affords permanent hair coloring. However, use of this conventional method does not provide maximum color deposition or retention and the range of color nuances especially in the red shades is limited.

The duration over which dyed hair remains colored is in principle only limited by the hair growth rate assuming the treatment does not affect the color of the hair as it is formed, i.e., the "roots". In practice dye films deposited on the hair are susceptible to extraction by repeated shampooing, erosion by combing and brushing, and fading by exposure to sunlight and oxygen. Red colors are particularly susceptible to these degrading processes and in an attempt to achieve sufficiently deep and long lasting red shades consumers often try to compensate by increasing the intensity of the initial color. However, this can lead to hair that has an unnatural or painted appearance.

The underlying problem in achieving vibrant and natural colors especially dark reds, that are also long-lasting and fade resistant, through oxidative dyeing of hair is that only a small portion of such colors enters the interior of the hair fiber during the dyeing process. As is well known, the color of oxidative dyes arises from the oxidative coupling of primary intermediates and secondary intermediate (often called couplers)—essentially dimerization and/or polymerization. Thus, oxidative coupling leads to an increase in molecular weight as well as an increase in conjugation. However, as the molecular weight rises, it becomes increasingly difficult for the polymerized dye to penetrate the hair fibers. Thus, the darkest colors are more likely to remain at the surface of the hair fibers where they are most susceptible to erosion, and abrasion. Being on the outside of the fibers these colors are also in an "optical environment" that is least similar to the environment of the natural melanins in hair, i.e., dispersed within the hair fiber matrix. The term "painted" often used to describe the unnatural appearance of darkly dyed hair is more than coincidental!

One objective of the present invention of the invention is a method of coloring the hair, especially coloring hair a reddish color that will provide a more vibrant and natural looking color.

An additional objective is a method of coloring the hair that will provide greater resistance to erosion, abrasion and chemical fading.

A still further objective is to provide a convenient kit that can be used by individual consumers to practice the method at home.

These and other objectives will become clear from the description of the invention.

The following patents and publications have been considered:

U.S. Pat. No. 2,934,396 discloses a two-step process for coloring the hair utilizing an acid solution of 5,6 dihydroxyindole followed by application of a solution containing an oxidizing agent.

U.S. Pat. No. 3,194,734 discloses a two-step process for coloring the hair utilizing an acid solution of 5,6 dihydroxyindole derivatives followed by application of a solution containing an oxidizing agent.

U.S. Pat. No. 4,104,021 discloses successive applications of a mixture of coupler (aromatic primary amines and aminophenols) and an oxidizing agent with each treatment having an increased level of oxidizing agent.

U.S. Pat. No. 4,370,142 discloses the dyeing of hair with a mixture of para-phenylenediamine, ortho-aminophenol, and hydrogen peroxide.

GB 2205329 A discloses a process comprising treating hair with a mixture of an oxidation base and iodide ions and subsequently treating hair with a solution of hydrogen peroxide at pH 2–12.

U.S. Pat. No. 4,804,385 discloses a process comprising treating hair with a mixture of an 5,6 dihydroxyindole and iodide ions and either subsequently or before treating hair with a solution of hydrogen peroxide.

U.S. Pat. No. 4,888,027 discloses a process comprising treating hair with a mixture of an 5,6 dihydroxyindole and iodide ions and subsequently treating the hair with an alkaline solution of hydrogen peroxide.

U.S. Pat. No. 5,173,085 discloses a process comprising treating the hair with an aqueous solution of a metal salt, followed or preceded by treatment with 5,6 dihydroxyindole, rinsing and finally treated with a aqueous solution of hydrogen peroxide.

EP 0755 669 B1 discloses a two step process wherein the hair is first treated with a solution containing magnesium ions followed by treatment with a mixture of an oxidation base and an oxidizing agent.

U.S. Pat. No. 5,980,586 discloses a process for dyeing the hair with a mixture of an aminoethanethiol, dihydroxybenzene, and a ferricyanide or persulfate.

WO 01/28508 A1 discloses a composition and method for coloring hair comprising an oxidizing agent, an oxidative or non-oxidative dye used in combination with ammonium carbonate or carbamate.

WO 02/02062 discloses the use of acid salts to increase the absorption qualities of anionic direct dyes in the coloring of fibers and a procedure for accomplishing this.

U.S. Pat. No. 5,525,123, discloses a hair dyeing composition based on oxidation dyestuff precursors at least one developer, coupling agent, metal salt, and an ammonium compound.

U.S. Pat. No. 5,279,620 discloses mixtures of oxidation colorants and certain indole coupler.

Co-owned and co-pending Ser. No. 09/811,920 filed Mar. 19, 2001, incorporated by reference herein, discloses a method for permanently dyeing hair which comprises subjecting hair to a number of treatments, having a set time interval between each of the two consecutive steps.

Co-owned and co-pending Ser. No. 10/075,745 filed February 14 2002, incorporated by reference herein, discloses a method for permanently dyeing hair which comprises contacting the hair with a substantially inactive mixture including one or more oxidation dyes followed by application of a developer which oxidizes the dye.

None of the references cited above teaches that a sequential method for coloring the hair in which specific dyes in a non-anionic, preferably nonionic, and substantially oxidatively inactive form are first contacted with the hair followed by a developer lead to more vibrant colors and more varied tones.

SUMMARY OF THE INVENTION

The subject invention provides a method for delivering more vibrant, natural and long-lasting color to hair utilizing specific dye precursor compositions at a specific state of ionization to achieve more vibrant and natural looking colors that are longer lasting and more shampoo and fade resistant.

More specifically, the method comprises carrying out the following sequential steps in the order indicated:
a) contacting the hair with a dye precursor mixture comprising:
   i) a primary intermediate having a pKa in the range from about 3 to about 10 selected from the group consisting of the neutral or salt forms of para-phenylenediamine, derivatized para-phenylenediamines, para-aminophenol, substituted para aminophenols, 4,5-diaminopyrazole, substituted 4,5-diaminopyrazole, polyamino-pyrimidine, hydroxy-polyaminopyrimidine, and other substituted polyaminopyrimidine and mixtures thereof,
   ii) an optional coupler having a pKa in the range from about 3 to about 10 wherein the pH of the precursor solution is selected such that less than 50% of the molecules comprising the primary intermediate and the coupler are in their anionic form when they first contact the hair, and
b) contacting the hair with a developer mixture capable of inducing oxidation of primary intermediate and coupler in the precursor mixture that is in contact with the hair to form colored species, wherein the dye precursor mixture remains in contact with the hair for a time period of from about 0.5 to 60 minutes before the hair is contacted with the developer and wherein the primary intermediate and coupler remain substantially inactive during this time period.

A second embodiment of the invention is a kit that allows individual consumers to conveniently practice the coloring method disclosed.

More specifically, the hair coloring kit comprises:
a) a dye precursor mixture comprising:
   iii) a primary intermediate having a pKa in the range from about 3 to about 10 selected from the group consisting of the neutral or salt forms of para-phenylenediamine, derivatized para-phenylenediamines, para-aminophenol, substituted para aminophenols, 4,5-diaminopyrazole, substituted 4,5-diaminopyrazole, polyamino-pyrimidine, hydroxy-polyaminopyrimidine, and other substituted polyaminopyrimidine and mixtures thereof,
   i) an optional coupler having a pKa in the range from about 3 to about 10 wherein the pH of the precursor solution is selected such that less than 50% of the molecules comprising the primary intermediate and the optional coupler are in their anionic form when they first contact the hair, and
b) a developer mixture capable of inducing oxidation of primary intermediate in the precursor mixture that is in contact with the hair to form colored species wherein the dye precursor mixture is capable of remaining in contact with the hair for a time period of from about 0.5 to 60 minutes before the hair is contacted with the developer and wherein the primary intermediate and coupler are capable of remaining substantially inactive during this time period.

DETAILED DESCRIPTION OF THE INVENTION

As used herein wt % refers to weight % of an ingredient as compared to the total weight percent of the composition that is being discussed. For example, when wt % is used to discuss the amount of an ingredient that is in the dye precursor mixture, this means weight % as compared to the total weight of the dye precursor mixture As used herein "inactive" or "substantially inactive" means that the oxidation hair dye precursors are not chemically reacting or are not chemically reacting to a substantial degree, so as to form coupled or polymerized hair color molecules, or it means that the oxidation hair dye precursors are not chemically reacting in a substantial manner so as to form coupled or polymerized hair color molecules.

Dye precursor mixtures refers generally to those compositions of the present invention which comprise oxidative hair dye precursors and are suitable for use on human hair, e.g., have the appropriate safety profile. Developer mixture refers generally to those compositions of the invention which are capable of inducing an oxidation reaction, a coupling reaction or a polymerization of the oxidative hair dye precursors that have been previously applied to the hair as part of the precursor mixture and are suitable for use on human hair. It should be understood that the latter step can be achieved by incorporating an active oxidizing agent in the developer mixture or by manipulating the pH or other chemical "environmental factor" to activate a nascent oxidizing agent that may already be present on the hair from contact with the precursor mixture.

The present invention relates to methods and compositions for achieving the permanent coloring of hair which methods comprise two key steps performed in sequence:
1) contacting the hair with a substantially inactive dye precursor mixture of at least one primary intermediate and at least one coupler for a period of about 30 seconds to about 60 minutes, followed by,
2) contacting the hair with a developer mixture capable of oxidizing the hair dye precursors applied with the precursor mixture, to react, dimerize and/or polymerize so as to form hair color molecules.

Without being bound by theory, it is believed that the above method provides the oxidation dye precursors with both the time and the chemical environment for diffusion into the hair shaft. The second step causes the formation of larger sized hair color molecules within the hair shaft. Because of their size, these hair color molecules have a lower tendency for diffusing out of the hair fibers. Because they are within the keratin matrix, they exhibit a more natural array of colors.

The compositions and methods of the present invention may be used to color different types of hair such as Asian hair and Caucasian hair.

It will be understood by those skilled in the art that concentrations of oxidative hair dye precursors which may be employed in the present invention can be varied depending upon, for example, the hair type which is to be colored and on the coloring effect which is desired.

What follows is a description of the ingredients that can be included in the mixtures and the means for carrying out the steps of the present invention.

Dye Precursor Mixture

The dye precursor mixture of the present invention includes oxidative hair coloring precursors (also called oxidation dyes). Such oxidative hair coloring agents are used in combination with oxidizing systems, i.e., the developer, of the present invention to deliver color to the hair.

The dye precursor mixture also can contain ingredients used to enhance the solubility of the precursors in a predominantly aqueous medium ("solubility enhancers"). The mixture can also contain agents to control the pH so as to provide an optimal chemical environment for the precursors to interact with hair fibers ("pH control agents").

Oxidative Dyes

Permanent hair dye compositions as defined herein are compositions, which once applied to the hair, are substantially resistant to washout and abrasion.

The dye forming intermediates used in oxidative dyes can be aromatic diamines, naphthols, aminophenols, polyhydroxybenzenes, and their derivatives. These dye forming intermediates can be classified as; primary intermediates, and couplers (often also referred to as either secondary intermediates or modifiers). As used herein the term "precursor" means precursor, coupler, modifier, or intermediate and the like. Primary intermediates are chemical compounds, which by themselves will form a dye upon oxidation. The coupler or secondary intermediate is used with other intermediates for specific color effects or to stabilize the color.

At least two types of oxidative dyes are used in the invention: one type is a primary intermediate while the other type is a coupler.

Primary intermediates which are suitable for use in the compositions and processes herein include aromatic diamines, naphthols, polyhydric phenols, aminophenols and derivatives of these aromatic compounds (e.g., N-substituted and/or C— substituted derivatives of the amines, O— substituted and/or C— substituted derivatives of phenols).

Primary oxidation dye intermediates are generally colorless molecules prior to oxidation. Color is generated when the primary intermediate is 'activated' and subsequently joined with a secondary intermediate (coupling agent), which is also generally colorless, to form a colored, conjugated molecule. In general terms, oxidation hair dye precursors or intermediates include those monomeric materials which, on oxidation, form oligomers or polymers having extended conjugation systems of electrons in their molecular structure.

Because of the new electronic structure, the resultant oligomers and polymers exhibit a shift in their electronic spectra to the visible range and appear colored. For example, oxidation dye precursors capable of forming colored polymers include materials such as p-phenylenediamine, which has two functional groups, and are capable of oxidative polymerization to yield higher molecular weight colored materials having extended conjugated electron systems.

Preferred primary intermediates and couplers have a pKa in the range from about 3 to about 10, preferably between about 5 and about 10. The term pKa has it usual chemical definition: the negative logarithm of the acid dissociation constant, i.e., $PK_a = -\log_{10} K_a$. Thus a pKa of 5 corresponds to an acid dissociation constant of $10^{-5}$.

In a preferred embodiment of the invention, the pH of the dye precursor mixture is adjusted such that less than 50%, preferably less than 25% and most preferably less than 10% of the molecules comprising the dye precursors, i.e., the primary intermediate and coupler, are in their anionic form when in contact with the hair during the time period before the developer is applied. For example, if the precursor contains both an amine and an alcohol group, the pH should be below the pKa of the hydroxyl group of the alcohol. It has been found that this pH environment leads to a higher retention of dye precursor within the hair fiber and the high retention of color.

In an even more preferred embodiment of the invention, the pH of the dye precursor mixture is adjusted such that more than 50%, preferably more than 75% and most preferably more than 90%, of the molecules comprising the dye precursors, i.e., the primary intermediate and coupler, are in their neutral forms when in contact with the hair during the time period before the developer is applied. For example, if the precursor is an amine, the pH should be above the pKa of the conjugate acid of the amine precursor, e.g., an ammonium group. If the precursor contains both an amine and an alcohol group, the pH should be above the pKa of the conjugate acid of the amine but below the pKa of the hydroxyl group. It has been found that this pH environment leads to a still higher retention of dye precursor within the fiber and the highest retention of color.

Color modifiers (couplers), such as those detailed hereinafter, are preferably used in conjunction with the oxidation dye precursors herein and are thought to interpose themselves in the colored polymers during their formation and to cause shifts in the electronic absorption spectra thereof, thereby resulting in color changes. A representative list of oxidation dye precursors (primary intermediates and couplers) suitable for use herein is found in Sagarin, "Cosmetic Science and Technology", Interscience, Special Edition, Volume 2, pages 308 to 310 which is herein incorporated by reference.

The typical aromatic diamines, polyhydric phenols, aminophenols, and derivatives thereof, described above as primary dye precursors can also have additional substituents on the aromatic ring, e.g. halogen, alkyl, alkyl substituted additional substituents on the amino nitrogen, on the phenolic oxygen, or on the aromatic carbon, e.g. substituted and unsubstituted alkyl and aryl groups.

The hair coloring compositions of the present invention may, in addition to the essential oxidative hair-coloring agents, optionally include non-oxidative and other dye materials. Optional non-oxidative and other dyes suitable for use in the hair coloring compositions and processes according to the present invention include semi-permanent, temporary and other dyes. Non-oxidative dyes as defined herein include the so-called 'direct action dyes', metallic dyes, metal chelate dyes, fiber reactive dyes. Numerous examples of these and other synthetic and natural materials can be found in the compendium "Chemical and Physical Behaviour of Human Hair" 3rd Edn. by Clarence Robbins (pp 250–259); 'The Chemistry and Manufacture of Cosmetics'. Volume IV. 2nd Edn. Maison G. De dyes. Various types of non-oxidative dyes are detailed in: Navarre at chapter 45 by G. S. Kass (pp 841–920); 'Cosmetics: Science and Technology' 2nd Edn, Vol. 11 Balsam Sagarin, Chapter 23 by F. E. Wall (pp 279–343); 'The Science of Hair Care' edited by C. Zviak, Chapter 7 (pp 235–261) and 'Hair Dyes', J. C. Johnson, Noyes Data Corp., Park Ridge, U.S.A. (1973), (pp 3–91 and 113–139). The above articles are hereby incorporated by reference.

Specific hair dyes which may be included in the compositions as the primary intermediate includes: 3-methyl-p-aminophenol; 2,3-dimethyl-p-aminophenol; p-phenylene diamine, p-toluenediamine; 2-chloro-p-phenylenediamine; N-phenyl-p-phenylenediamine; N-2-methoxyethyl-p-phenylenediamine; N,N-bis-(hydroxyethyl)-p-phenylenediamine; 2-hydroxymethyl-p-phenylenediamine; 2-hydroxyethyl-p-phenylenediamine; 4,4'-diaminodiphenylamine; 2,6-dimethyl-p-phenylenediamine; 2-isopropyl-p-phenylenediamine; N-(2-hydroxypropyl)-p-phenylenediamine; 2-propyl-p-phenylenediamine; 1,3-di-(p-N,N-bis-(2-hydroxyethyl)-aminoanilino)-2-propanol; 2-methyl-4-dimethylaminoaniline; p-aminophenol; p-methylaminophenol; 2-hydroxymethyl-p-aminophenol; 2-methyl-p-aminophenol; 2-(2-hydroxyethylaminomethyl)-p-aminophenol; 2-methoxymethyl-p-aminophenol; and 5-aminosalicylic acid; catechol; pyrogallol; o-aminophenol; 2,4-diaminophenol; 2,4,5-trihydroxytoluene; 1,2,4-trihydroxybenzene; 2-ethylamino-p-cresol; 2,3-dihydroxynaphthalene; 5-methyl-o-aminophenol; 6-methyl-o-aminophenol; and 2-amino-5-acetaminophenol; 2,5-diaminotoluene; 2-dimethylamino-5-aminopyridine; -tetra-aminopyrimidine; 4,5-diamino-1-methylpyrazole; 4,5-diamino-1-hydroxyethyl pyrazole, 6-methoxy-8-aminoquinoline; 2,6-dihydroxy-4-methylpyridine; 5-hydroxy-1,4-benzodioxane; 3,4-methylenedioxyphenol; 4-hydroxyethylamino-1,2-methylenedioxybenzene; 5-chloro-2,3-dihydroxypyridine; 2-hydroxyethylamino-6-methoxy-3-aminopyridine; 3,4-methylenedioxyaniline; 7-hydroxyindole; 5-hydroxyindole; 2-bromo-4,5-methylenedioxyphenol; 3-amino-2-methylamino-6-methoxypyridine; 2-amino-3-hydroxypyridine; 4-hydroxy-2,5,6-triaminopyrimidine, 5-hydroxyindoline, 7-hydroxyindoline or combinations thereof.

Preferred primary intermediates for use in the invention include: p-phenylenediamine; p-aminophenol; N,N-bis(2-hydroxyethyl)-p-phenylenediamine; 2,5-toluenediamine; 2-methyl-p-aminophenol; 3-methyl-p-aminophenol; 2,3-dimethyl-p-aminophenol, p-methylaminophenol; 4,5,-diamino-1-hydroxyethyl pyrazole, 2,4,5,6-tetra-aminopyrimidine; 4-hydroxy-2,5,6-triaminopyrimidine o-aminophenol; and mixtures thereof.

The most preferred primary intermediates are p-phenylenediamine, p-aminophenol, 3-methyl-p-aminophenol; N,N-bis(hydroxyethyl)-p-phenylenediamine, 2,5,-toluenediamine, o-aminophenol, and mixtures thereof.

The primary intermediate is generally present in the precursor mixture at a level from about 0.005 wt % to about 10 wt %, preferably from about 0.01 to about 5 wt %, and most preferably from about 0.01 to about 4 wt %.

The coupler (or secondary intermediate) is utilized to expand the color range by copolymerization with the primary intermediate. These materials can also accelerate color formation.

Specific hair dye intermediates that can be used as couplers in the present invention include: m-aminophenol; 2-methyl-1-naphthol; 1-acetoxy-2-methylnaphthalene; resorcinol; 4-chlororesorcinol; 1-naphthol; 1,5-dihydroxynaphthalene; 2,7-dihydroxynaphthalene; 2-methylresorcinol; 1-hydroxy-6-aminonaphthalene-3-sulfonic acid; thymol (2-isopropyl-5-methylphenol); 2-chlororesorcinol; 2,3-dihydroxy-1,4-naphthoquinone; and 1-naphthol-4-sulfonic acid; m-phenylenediamine; 2-(2,4-diaminophenoxy)ethanol; N,N-bis(hydroxyethyl)-m-phenylenediamine; 2,6-diaminotoluene; N,N-bis(hydroxyethyl)-2,4-diaminophenetole; bis (2,4-diaminophenoxy)-1,3-propane; 1-hydroxyethyl-2,4-diaminobenzene; 2-amino-4 hydroxyethylaminoanisole; aminoethoxy-2,4-diaminobenzene; 2,4-diaminophenoxyacetic acid; 4,6-bis(hydroxyethoxy)-m-phenylenediamine; 2,4-diamino-5-methylphenetole; 2,4-diamino-5-hydroxyethoxytoluene; 2,4-dimethoxy 1,3-diaminobenzene; and 2,6-bis(hydroxyethylamino)toluene; 2-hydroxy-4-carbamoylmethylaminotoluene; m-carbamoylmethylaminophenol; 6-hydroxybenzomorpholine; 2-hydroxy-4-aminotoluene; 2-hydroxy-4-hydroxyethylaminotoluene; 4,6-dichloro-m-aminophenol; 2-methyl-m-aminophenol; 2-chloro-6-methyl-m-aminophenol; 2-hydroxyethoxy-5-aminophenol; 2-chloro-5-trifluoroethylaminophenol; 4-chloro-6-methyl-m-aminophenol; N-cyclopentyl-3-aminophenol; N-hydroxyethyl-4-methoxy-2-methyl-m-aminophenol and -methoxy-2-methylphenol; 1-phenyl-3-methyl-5-pyrazolone; 5-hydroxy-1,4-benzodioxane; 2,6-dihydroxy-3,4-dimethylpyridine; 3,5-diamino-2,6-dimethoxypyridine; 2,6-bis-hydroxyethoxy-3,5-diaminopyridine; 3-amino-5-hydroxy-2,6-dimethoxypyridine; 4-hydroxyindole; 6-hydroxyindole; 2,6-diaminopyridine; 5-(3,5-diamino-2-pyridyloxy)-1,3-dihydroxypentane; 3-(3,5-d iamino-2-pyridyloxy)-2-hydroxypropanol, 4-hydroxyindoline, 6-hydroxyindoline, and combinations thereof.

Preferred couplers for use in the invention include: resorcenol; m-aminophenol; 5-amino-2-methylphenol; 2-methyresorcinol, 1-n-naphthol; 2-methyl-1-naphthol; 2-( 2,4-diamino-phenoxy)ethanol; 1-phenyl-3-methyl-5-pyrazolone; m-phenylenediamine; 4-hydroxyindole, 6-hydroxyindole; 4 chlororesorcinol; 2-chlororesorcinol, 2,6-diaminotoluene, 4-hydroxyindoline, 6-hydroxyindoline, 2,6-diaminopyridine, 2-methyl-5-hydroxyethylaminophenol, and mixtures thereof.

The most preferred couplers are o-aminophenol, 1-naphthol; 2-methylresorcinol; resorcinol; m-aminophenol; 5-amino-2-methylphenol; 2(2,4-diaminophenoxy)-ethanol; m-phenylenediamine; 1-phenyl-3-methyl-5-pyrazolone; 2,6,-diaminopyridine and mixtures thereof.

The coupler is generally present in the precursor mixture at a level from about 0.005 wt % to about 10 wt %, preferably from about 0.01 to about 5 wt %, and most preferably from about 0.01 to about 4 wt %.

The weight ratio of primary intermediate to coupler is generally in the range from about 100 to about 0.01, preferably from about 50 to about 0.05 and most preferably from about 10 to about 0.1.

It should be understood that the descriptions of primary intermediates and couplers given above is meant implicitly include the salt forms of those dye molecules that form stable salts. For example, the hydrochloride or sulfate salts in the case of amines, and the alkali metal salts in the case of phenols.

Solubility Enhancers

Water is the preferred principal solvent, carrier or diluent for the compositions according to the present invention. As such, the compositions according to the present invention may include one or more solubility enhancers as defined above. Generally, two preferred classes of solubility enhancers are solvents and surfactant systems.

Preferred solvents are miscible with water and innocuous to the skin. Solvents suitable for use herein include $C_1$–$C_{10}$ mono- or polyhydric alcohols and their ethers, glycerine, with monohydric and dihydric alcohols and their ethers. In these compounds, alcoholic residues containing 2 to 6 carbon atoms are preferred. Thus, a particularly preferred group includes ethanol, isopropanol, n-propanol, butanol, propylene glycol, ethylene glycol monoethyl ether, hexylene glycol and mixtures thereof.

The solvents may be present in the precursor mixture at a level of from about 0.1 to 20 wt %, preferably from about 0.1 to about 15 wt % and most preferably from about 0.5 to 10 wt %.

The second class of solubility enhancer useful in the present invention is surfactants.

A particularly suitable class of surfactants is cationic surfactants. One type of preferred cationic surfactant is amine based and includes alkyl amines, alkylethoxy amines, ethoxylated alkyl amines and alkyl alkanol amines. Preferred alkyl groups have 1 to about 22 carbon atoms and can have a mixture of chainlengths, e.g, methyl and hexadecyl. The term amines include primary, secondary, tertiary and quaternary amines.

A second type of preferred cationic surfactant is amidoamines and includes C12–C22 alkyl or alkylethoxy mono, di and higher (poly)amidoamines which can be ethoxylated or unethoxylated. Examples include sodium dimethylaminopropyl coco-aspartamide, cocoamidopropyl dimethylamine, olivamidopropyl dimethylamine, soyamidopropyl dimethylamine, tallowamidopropyl dimethylamine, stearamidoethyl dimethylamine and mixtures thereof.

Another preferred class of surfactant that is suitable for use as a solubility enhancer is nonionic surfactants. This class includes long chain fatty alcohols, mono, di and triglyceride and their derivatives, long chain (C12–C18) alcohol ethoxylates and mixtures thereof. Examples include: steareth 20, oleth 10, laureth 4, PEG-12 glyceryl dioleate, glycerol stearate, sorbitan oleate, PPG-9 buteth-12 and mixtures thereof.

The level of surfactants used as solubility enhancers in the dye precursor mixture can generally range from 0.1 to about 30 wt %, preferably from about 0.2% to about 20 wt % and most preferably from about 0.25 to about 15 wt %.

Both solvents and surfactants can and often are combined to achieve the desired state of solubility of the primary intermediate and coupler in the dye precursor mixture. However, it has been found that the type and level of solubility enhancer affect the ability of the oxidative dyes to absorb into the hair fibers and be retained after development. Although this can be difficult to predict, the optimum type and level of solubility enhancer can be determined empirically by treating a standard hair sample under controlled conditions with a precursor mixture and developing the color with an oxidizing agent. One such test protocol is the Piedmont In-Vitro Color Test and is described below. As discussed below, ΔE is the distance between two colors in the Tristimulus color space. Thus, ΔE is the change in color of the test hair sample after treatment with the precursor solution and development with a standard oxidizing agent. It has been found that the level and type of solubility enhancer used in the precursor solution should be such that this mixture provides a color change, ΔE, of at least about 0.15 when measured by the in-vitro Piedmont Color Retention Test described below.

Nascent Oxidizing Agents

In a second embodiment of the invention a nascent oxidizing agent is incorporated in the precursor mixture that is applied to the hair in the first step. By nascent oxidizing agent is meant oxidizing agents that are potentially capable of initiating oxidative coupling and color reaction, but because of the chemical environment provided by the precursor solution, are rendered substantially inert.

An example of such a nascent oxidizing agent is hydrogen peroxide when present in a solution that has a pH less than about 4, preferably a pH between from about 2 to about 4. However, if a developer solution containing an alkaline buffering agent at a sufficient level is mixed with such a precursor solution the pH increases to a value greater than 7 where the hydrogen peroxide becomes active and initiates dye coupling and color formation.

When nascent oxidizers are used, it is preferred to adjust the precursor mixture to maintain the precursors not in their anionic forms (most preferably in their neutral forms) and substantially inert to oxidative coupling. This may require the incorporation of reversible oxidation inhibitors.

Developer Mixture

The developer mixture comprises ingredients capable initiating the chemical coupling or polymerization of the oxidative dye precursors which gives rise to the desired hair color. The hair color developer compositions of the invention may have a preferred pH in the range of from about 8.0 to about 11, more preferably from about 9.0 to about 10.5. To achieve this, the developer mixture also generally contains an alkaline pH control agent and may also contain other ingredients in an aqueous base.

There are two preferred embodiments of developer mixture of the instant invention. In one embodiment, the developer comprises an active oxidizing compounds capable of inducing oxidation of the precursors that are in contact with the hair so as to form colored species.

In the second preferred embodiment the developer is capable of changing the chemical environment when applied to the hair already in contact with the precursor mixture so as to activate a nascent oxidizing agent present in said precursor mixture. This activation induces oxidation and reaction of the primary intermediate and coupler to form hair color species. Nascent oxidizing agents have already been described above. A preferred route to change chemical environment is to induce a change in pH by incorporating an appropriate pH control agent in the developer mixture. A preferred route is by incorporation of an alkaline pH control agent capable of increasing the pH of the dye precursor environment on the hair.

It is sometimes convenient to incorporate hair conditioning into the developer mixture or the separate packages that are mixed before use to generate the developer. This practice can avoid extra process steps and leave the hair manageable and having a desirable feel. However, when this is carried out it is critical to ensure that the conditioning agents are selected so as not to interfere with the oxidation step, for example, by not promoting wasteful decomposition. It is also necessary to select a conditioner that can function, i.e., adsorb on the hair, at the pH of the developer mixture on the hair.

Suitable active oxidizing compounds and alkaline pH control agents are discussed below.

Active Oxidizing Compounds

The oxidizing compounds or agents useful in the methods and compositions of the present invention are generally inorganic peroxygen materials capable of yielding peroxide in an aqueous solution. Inorganic peroxygen oxidizing agents are well known in the art and include hydrogen peroxide, inorganic alkali metal peroxides such as sodium periodate, sodium perbromate and sodium peroxide, and inorganic perhydrate salt oxidizing compounds, such as the alkali metal salts of perborates, percarbonates, perphosphates, persilicates, persulphates and the like. These inorganic perhydrate salts may be incorporated as monohydrates, tetrahydrates etc. Also useful are melamine peroxide, sodium perborate, and sodium percarbonate. Mixtures of two or more of such inorganic peroxygen oxidizing agents can also be used. For all of these compounds, the active material is active hydrogen peroxide. One skilled in the art would recognize how much active hydrogen peroxide is desired in the hair coloring compositions that are being formulated and therefore one skilled in the art would be able to calculate how much of a peroxygen compound, such as for example, melamine peroxide, to employ.

pH Control Agents

The dye precursor mixture and developer compositions of the present invention may have widely ranging pH values. When bases are present in compositions of the invention, the pH can range from about 7.0 to about 11.0, preferably 9 to 10.5. Acidic pH can range from about 3 to 7, preferably 5 to 7, and may be employed in those embodiments of the present invention wherein oxidation hair dye precursors are applied to the hair in admixture with nascent oxidizing compounds such as hydrogen peroxide. As already mentioned this is done because such low pH's will stabilize the hydrogen peroxide present and substantially suppress the color forming oxidation reaction.

pH adjustment can be effected by using well known acidifying agents or acidic buffering agents in the field of treating keratinous fibers, and in particular human hair. Such acidic pH control agents include inorganic and organic acids such as hydrochloric acid, tartaric acid, citric acid, and carboxylic or sulphonic acids such as ascorbic acid, acetic acid, adipic acid, lactic acid, sulphuric acid, formic acid, ammonium sulphate and sodium dihydrogenphosphate/phosphoric acid, disodium hydrogen phosphate/phosphoric acid, potassium chloride/hydrochloric acid, potassium dihydrogen phthalate/hydrochloric acid, sodium citrate/hydrochloric acid, potassium dihydrogen citrate/hydrochloric acid, potassium dihydrogencitrate/citric acid, sodium citrate/citric acid, sodium tartarate/tartaric acid, sodium lactate/lactic acid, sodium acetate/acetic acid, disodium hydrogenphosphate/citric acid and sodium chloride/glycine/hydrochloric acid and mixtures thereof.

Still other organic acids include maleic acid, malic acid, succinic acid, glycolic acid, glutaric acid, benzoic acid, malonic acid, salicylic acid, gluconic acid, polyacrylic acid, their salts, and mixtures thereof.

Especially preferred acidic pH control agents for use in the dye precursor and developer compositions include citric acid, lactic acid, glycolic acid, acetic acid, phosphoric acid and mixtures thereof.

Several different basic pH control agents can be used to adjust the pH of dye precursor and developer mixtures of the present invention (both in storage and at point of use). Nonlimiting examples of suitable basic buffering agents are ammonium hydroxide, urea, ethylamine, dipropylamine, triethylamine and alkylenediamines such as 1,3-diaminopropane, anhydrous alkaline alkanolamines such as, mono or di- or tri-ethanolamine, preferably those which are completely substituted on the amine group such as dimethylaminoethanol, polyalkylene polyamines such as diethylenetriamine or a heterocyclic amine such as morpholine as well as the hydroxides of alkali metals, such as sodium and potassium hydroxide, hydroxides of alkali earth metals, such as magnesium and calcium hydroxide, basic amino acids such as L-arginine, lysine, oxylysine and histidine aminoalkylpropanediol, and mixtures thereof.

Certain alkaline buffering agents such as ammonium hydroxide and monoethanolamine (MEA), urea and the like, can also act as hair swelling agents (HSA's).

Preferred alkaline or basic pH control agents for the dye precursor and developer compositions according to the present invention, is ammonium hydroxide and/or sodium hydroxide.

The level of pH control agent used in either the dye precursor or developer mixture can generally range from a value of about 0.2 wt % to about 20 wt %, preferably from about 0.5 to about 18 wt % and most preferably from 1 to about 15 wt %.

In hair coloring kits of the invention which contain the hair colorant compositions, i.e., the oxidation precursors, of the present invention and the hair color developer compositions of the present invention, a portion of peroxide oxidizing agent, may be present in either solid or liquid form, such as hydrogen peroxide, and an acid buffering agent solution as mentioned above may be required to stabilize the hydrogen peroxide. Since hydrogen peroxide is stable in the pH range from 2 to 4, it may be necessary to use a buffering agent having a pH within this range. Dilute acids are suitable as hydrogen peroxide buffering agents. Phosphoric acid is a preferred agent for buffering hydrogen peroxide solutions.

Thickeners

Thickeners may be optionally included in the oxidation hair colorant compositions and hair developer compositions of the invention, and specifically thickeners may be included in the hair dye precursor part and the hair color developer parts of the invention. Long chain fatty alcohols having from about 11 to about 22 carbon atoms in the long fatty chain can be thickener constituents of the compositions of this invention. These alcohols can be used alone, or in admixture with each other. When included in the compositions, the alcohol is preferably present at from about 0.5 to about 10 weight percent of the composition, and more preferably at from about 2 to about 8 weight percent.

Lauryl alcohol, oleyl alcohol, myristyl alcohol, stearyl alcohol, behenyl alcohol and the like, and mixtures thereof are contemplated herein as thickeners. In addition, mixtures of natural or synthetic fatty alcohols having fatty chain lengths of from about 11 to about 18 carbons are also useful. Several such mixtures are available commercially, and are exemplified by the material containing a mixture of synthetic alcohols with 12 to 15 carbons in the alkyl chain sold under the trademark NEODOL 25 by Shell Chemical Company, and the material containing a mixture of synthetic alcohols with chain lengths of 12 to 16 carbons sold under the trademark ALFOL 1216 Alcohol by Conoco Chemicals.

Thickening agents suitable for use in the compositions herein may also be selected from oleic acid, cetyl alcohol, oleyl alcohol, sodium chloride, cetearyl alcohol, stearyl alcohol, synthetic thickeners such as CARBOPOL, ACULYN 28, STRUCTURE 2001, 3001, and XL, and ACROSYL and mixtures thereof. Preferred thickeners for use herein are ACULYN 22 (RTM), steareth-20 methacrylate copolymer; ACULYN 44 (RTM) polyurethane resin and ACUSOL 830 (RTM), acrylates copolymer that are available from Rohm and Haas, Philadelphia, Pa., USA. Additional thickening agents suitable for use herein include sodium alginate or gum arabic, or cellulose derivatives, such as methylcellulose or the sodium salt of carboxymethylcellulose or acrylic polymers.

Fatty alcohols of the above discussed carbon chain lengths which are ethoxylated to contain an average of one or two moles of ethylene oxide per mole of fatty alcohol can be used in place of the fatty alcohols themselves. Examples of such useful ethoxylated fatty acids include ethylene glycol cetyl ether, polyoxyethylene (2) stearyl ether, and the like; the exemplary compounds having CTFA Dictionary names of Ceteth-1 and Steareth-2, respectively.

Other Optional Ingredients

The dye precursor compositions and developer compositions of the present invention can comprise a wide range of optional ingredients. Examples of these functional classes include: mildness enhancers such as cholesterol and its derivatives, hair swelling agents, anticaking agents, antioxidants, binders, biological additives, bulking agents, chelating agents, chemical additives, colorants, cosmetic astringents, cosmetic biocides, denaturants, drug astringents, emulsifiers, film formers, fragrance components, humectants, opacifying agents, plasticizers, preservatives, propellants, reducing agents, solvents, foam boosters, hydrotropes, solubilizing agents, suspending agents (nonsurfactant), sunscreen agents, ultraviolet light absorbers, and viscosity increasing agents (aqueous and nonaqueous), and hair fiber lubricants. Examples of other functional classes of materials useful in the art include solubilizing agents, sequestrants, amino acids, ingredients that impart shine, hydrolysed proteins and the like.

It may also be advantageous to include agents that condition the hair to improve combability and impart a silky/moisturized feel to the hair after it dries. Such agents include fatty long chain amines and their derivatives, silicones such as dimethicone and amodimethicone, long chain fatty acohols and mixtures of these materials. Such conditioners can be incorporated in either the precursor mixture, the developer mixture Conditioners can also be packaged separately when kits are employed.

Other Optional Steps

Aligning Means

"Aligning and distributing means of the invention" is used interchangeably with "aligning and distributing means" or simply "aligning means" and refers to a means or implement employed to align the hair and distribute the dye precursor after the dye precursor is applied to the hair but before the hair is contacted with the developer mixture.

An optional step that can be incorporated in the process is the application of means for aligning the hair after it has been in contact with the precursor mixture for a period of time but before the developer is applied. Without being bound by theory, it is believed that this step performs two key functions. First, during the process of hair alignment, excess precursor solution that tends to collect at hair fiber junctions by capillary forces, is distributed uniformly over the hair, which provides a more even tone and avoids blotchiness. Second, the process of alignment "opens" the hair fiber assembly to make it readily and more uniformly accessible to the developer solution. Another advantage of including an alignment and distributing means is that it can potentially provide highlights by careful selection of its design.

A variety of implements can serve as an aligning means in the invention. These includes combs and picks, brushes, sponges, towlettes, and various modifications and combinations of these basic elements that are known in the art.

Alignment means that have at least one comb or one brush element are especially preferred. The comb is an implement of grooming dating from ancient times yet patents on various improvements continue to appear. As used here a comb element consists of strip of material (e.g., plastic) to which are fixed one or more rows of teeth. The comb element can be of simple construction or it can be contoured or have features that induce highlighting, for example, variable spacing or length of the teeth or wells cut into the fixing strip.

Optionally, the comb element can also incorporate absorbent features that additionally remove excess dye or a portion of excess dye precursor solution that has not penetrated the hair. Such "drying combs" are well known in the art. For example, U.S. Pat. No. 4,013,086, incorporated by reference herein, discloses a combing device that accommodates disposable absorbent sheet sandwiched between its split teeth. An alternative means for incorporating an absorbent material is disclosed in U.S. Pat. No. 1,166,361, incorporated by reference herein. Wingard in U.S. Pat. No. 4,421,129 incorporated by reference herein, and the references incorporated therein describes still other combination aligning and drying combs.

A brush element as defined herein is an aligning means that has bristles set into a handle. The handle can be rigid or flexible. The bristles can be single rigid filaments or tines, flexible fibers, or tufts of fibers. The bristles can be of uniform length or they can be of different lengths either to allow the brush element to promote highlighting effects by opening channels or different depths or to allow the brush to be contoured to conform to the shape of the head. The brush can also incorporate step features which further promote highlighting, such as is disclosed in U.S. Pat. No. 6,453,909 B1, incorporated by reference herein. Further, the bristles can be distributed in rows in a planar configuration or radially distributed to form an arc.

Preferred brush elements are comprised of a planar plastic base to which rows of rigid plastic tines are affixed as these are simple and inexpensive to manufacture.

The brush element can also incorporate an absorbent feature that performs the secondary function of removing excess dye precursor solution that has not penetrated the hair fibers. For example, the brush can incorporate a hydrophilic foam pad, or other absorbent material such as a nonwoven sheet. U.S. Pat. No. 4,856,541, and U.S. Pat. No. 5,002,075, both incorporated by reference herein, describes brushes that incorporate a hydrophilic polyurethane foam affixed on the handle at the base of the tines.

Both the comb and brush elements can be constructed of materials that can also assist in the absorption of excess dye precursor solution. Examples of absorptive plastic materials of construction that are known to aid drying are disclosed in U.S. Pat. No. 3,992,336, U.S. Pat. No. 4,018,729, and U.S. Pat. No. 4,421,129, all incorporated by reference herein.

Towelettes, and clothes, are still other types of implements that can serve as aligning means especially in markets where low cost is an important issue. These can be of woven or non-woven construction, and be planar or contoured to fit the fingers or hand (e.g., in the form of gloves). Such implements can also incorporate textured surfaces that promote alignment of the hair fibers.

Sponges or foams can also serve as an aligning implement and additionally incorporate a handle element. These implements can range from planer sheets to various contour shaped articles and comprise small cells or large open cells with diamond shaped faces.

A still further type of implement can be of the type described in U.S. Pat. No. 6,138,376, incorporated by reference herein, for the passive drying of hair. This device consists of two elongated elements coupled in a open/close relationship (analogous to a closes—pin) which can used to align the hair. Again this element can incorporate an absorbent element that removes excess dye precursor while performing the primary function of aligning the hair.

The aligning means can also comprise a combination to the above-described elements. Combinations of brush and comb elements are well known in the art and an early example may be found in U.S. Pat. No. 660,893.

The aligning means described above can also incorporate a means for dispensing either the dye precursor mixture, the developer or both so as to achieve a simple to use system. Examples of potential systems are provided in U.S. Pat. No. 6,505,983 B1, U.S. Pat. No. 5,975,089, U.S. Pat. No. 5,024,243, and U.S. Pat. No. 6,260,557 all incorporated by reference herein.

Regardless of whether the aligning means is a separate implement or part of an integrated system, it is applied to the hair between the application of the dye precursor mixture and the application of the developer, i.e., after the hair is contacted with the dye precursor (including any nascent oxidizing agent when desired) but before the hair is contacted with the developer. The time interval between contacting the hair with dye precursor and alignment of the hair is generally between 30 seconds to about 60 minutes, preferably 5 minutes to 45 minutes and most preferably between 10 minutes 5' and 30 minutes.

APPLICATION OF METHODS AND COMPOSITIONS OF THE INVENTION

The dye precursor and hair color developer parts of the present invention are applied sequentially to the hair. Optionally, a means is applied to the hair for aligning the hair fibers and distributing the precursor mixture, i.e., after the hair is contacted with the dye precursor part, a period of about 30 seconds to about 60 minutes is allowed to elapse after which the alignment means is applied to the hair. In this case, the developer is typically applied 0.5 to 20 minutes after the hair alignment step. The alignment and distributing means can be a comb, a brush, a disposable towellete, and a sponge like device (large or small cells) or a device that comprises a combination of these elements or in further combination with a dispensing means as described above. The consumer can supply the alignment and distributing means or it can be a specialized tool provided as part of the kit alone.

The process described above is in sharp contrast to conventional permanent hair coloring methods which require that the hair be contacted with a dye precursor composition and a hair color developer composition, simultaneously or nearly simultaneously. Without being bound by theory, it is believed that an advantage of the methods of the present invention is that smaller hair dye precursor molecules are given time to diffuse into the hair shaft. Then when the hair is contacted with the hair color developer part, the smaller hair dye precursor molecules that are within the hair shaft undergo coupling and polymerization reactions so as to form larger color molecules that are trapped within the hair shaft because of their size. Another advantage of the methods of the present invention as compared to conventional permanent hair coloring methods, is that conventional permanent hair coloring methods cause much of the coupling and polymerization of the hair dye precursors to occur outside of the interior of the hair shaft and are wasted. Large hair color molecules are formed, and because of their size, these large hair color molecules cannot diffuse into the hair shaft.

The above physical phenomena can be described by the following chemical equations. When $$R_o/R_d \geq 1$$

where $R_o$ is the rate of oxidation of hair dye precursors and $R_d$ is the rate of diffusion of hair dye precursors, diffusion of hair color precursor into the hair fibers is limited by the rapid formation of dye molecules outside the hair fiber.

In contrast when $$R_o/R_d < 1$$

diffusion of hair color precursor becomes rate limiting and the dye precursors are able to penetrate the fibers to a greater extent.

Evaluation Methodology

Assessment of Initial Color and Color Change

The equipment used to measure both the initial color and color change on substrates (hair/skin) dyed with the singly packaged low pH coloring compositions of the present invention is a Hunter spectrophotometer. The value used to express the degree of color change induced by the combined treatment of precursor mixture and developer on any particular hair substrate is $\Delta E$. The term $\Delta E$, as defined herein, represents the distance in Tristimulus color space between two different samples, e.g., before and after treatment. $\Delta E$ is computed from the measured changes of the Tristimulus vales $\Delta L$, $\Delta a$, and $\Delta b$ values by:

$\Delta E$=difference of color of treated and non-dyed hair:
$$\Delta E=\sqrt{(\Delta L^2+\Delta a^2+\Delta b^2)}$$

where L is a measure of lightness and darkness (color intensity), wherein L=100 is equivalent to white, and L=0 is equivalent to black. Further, 'a' is a measure of the red and green quotients (color hues) such that positive equates to red and negative equates to green, and 'b' is a measure of the yellow and blue quotients (color hues) such that positive equates to yellow and negative equates to blue.

Piedmont In-vitro Color Retention Test

A 1 gm tress Piedmont hair from International Hair Products Inc. is first treated with the aqueous dye precursor composition at a level of between 1.5 to 3 gm precursor mixture per gm of hair. The precursor was distributed over the hair surface by means of a styling brush of the type commonly employed by salon stylists. After 20 minutes from the completion of the application of the precursor composition an aqueous developer solution (typically 1.5 gm to 3. gm per gm of hair) is then applied to the hair by means of a styling brush to develop the color. The hair tresses are dried overnight and the values of L, a, and b, are then measured and the change in color index, A E, of the tress compared to their initial value is then computed from the above equation.

It has been found that the color change produced by oxidative dyes can depend on the chemical environment provided by the precursor mixture when it comes into contact with the hair. Precursor mixtures useful in the present invention should at least be capable of producing a color change, $\Delta E$, of at least 0.15 units when used in the above test procedure.

When appropriate the above method can be modified to include an aligning and distributing step interspersed between the application of the precursor and the application of the developer.

The resistance of the treatment to fading by for example shampoo treatment can also be measured in a similar way.

After the above dye treatments, the dried hair tresses are placed in a tube containing a 10% shampoo solution and agitated for 1 hour by means of a mechanical shaker. The tresses are then rinsed and dried. The values of L, a, and b, are then measured and the change in color index, $\Delta E$, is computed and compared to their value before shampoo extraction or to the initial untreated hair as desired.

EXAMPLES

The following examples are shown as illustrations only and are not intended to limit the scope of the invention.

The examples just below show that the two step process of the present invention results in more vibrant hair color change that is more resistant to for example, shampooing. The compositions that are used just below were prepared for these laboratory tests and do not include ingredients such as for example fragrances that would ordinarily be employed in commercial compositions.

Example 1

Improvements in Color Vibrancy by Using 2-Step Dyeing Process—p-aminophenol and 5-amino-o-cresol.

A 2-gm Piedmont hair tress was treated with in a precursor mixture consisting of a solution of p-aminophenol (0.3%), 5-amino-o-cresol (0.35%), IPA (22.5%) in water (q.s. 100%) at pH 7 for 20 minutes according to the procedures outlined under Evaluation Methodology. Without rinsing, the hair was transferred to and kept in an aqueous alkaline developer solution consisting of hydrogen peroxide (2%) and $NH_4OH$ (0.56%) at pH 10 for an additional 25 minutes. The hair was finally rinsed and dried with a hair dryer.

In the control experiment, a similar 2-gm hair tress was dyed in a one step process by soaking in a solution comprising p-aminophenol (0.3%), 5-amino-o-cresol (0.35%), IPA (22.5%), hydrogen peroxide (2%) and $NH_4OH$ (0.56%), water q.s. (100%) for 45 minutes. This dye solution was freshly prepared immediately prior to introducing the hair tress. The hair was rinsed with water and dried with a hair dryer.

When the two tresses were presented to 10 panelists for color evaluation under controlled conditions, 90% of the panelists rated the color developed by the two step process as being more vibrant than the hair tresses treated by the conventional one step process.

Example 2

Illustration of the Improvement in Shampoo Resistance Using the 2-Step Process of the Present Invention An aqueous solution containing p-aminophenol (0.4%), 5-amino-o-cresol (0.45%), and IPA (22.5%) at pH 7 was used to treat Piedmont hair for 20 minutes as outlined in Example 1. The hair was transferred without rinsing to an aqueous alkaline solution consisting of hydrogen peroxide (3%) and $NH_4OH$ (0.56%) at pH 10 for an additional 25 minutes. The hair was finally rinsed and dried with a hair dryer.

A second set of tresses were dyed by the conventional method, using a freshly prepared solution containing p-aminophenol (0.4%), 5-amino-o-cresol (0.45%), IPA (22.5%), hydrogen peroxide (3%) and $NH_4OH$ (0.56%), water q.s. (100%) for 45 minutes.

After the above treatments both sets of dried hair tresses were agitated in a shampoo solution for an hour (see Evaluation Methodology), rinsed, dried, and their color measured.

It is seen from the Tristimulus color values recorded in Table 1 that the color developed by the 2-step process of this invention is about 43% more resistant to shampoo fading than the color of hair dyed by the conventional 1-step process (compare $\Delta E$).

TABLE 1

Comparison of shampoo resistance of hair dyed in p-aminophenol, 5-amino-o-cresol by 2-Step and conventional 1-Step process.

| Treatment | Changes in Tristimulus[a] values after shampooing | Changes in Color Index after shampooing |
|---|---|---|
| 2-Step process | $\Delta L = 2.48$<br>$\Delta a = -1.48$<br>$\Delta b = 1.43$ | $\Delta E = 3.22$ |
| Comparative example - 1-Step process | $\Delta L = 4.88$<br>$\Delta a = -2.69$<br>$\Delta b = 0.87$ | $\Delta E = 5.64$ |

Note
[a]$\Delta L$ represents the change in color intensity, $\Delta a$ represents the change in the ratio of red and green hue and $\Delta b$ represents the change in the ratio of yellow and blue hue of the color. $\Delta E$ is equal to the square root of the sum of the squares of $\Delta L$, $\Delta a$, and $\Delta b$.

Example 3

Illustration of the Improvement in Color Vibrancy and Shampoo Resistance Using the 2-Step Process of the Present Invention—3-methyl-4-aminophenol and 5-amino-o-cresol.

A 1-gm tress of Piedmont hair was treated with an aqueous isopropyl alcohol (37.5%) solution of 3-methyl-4-aminophenol (0.5%), 5-amino-o-cresol (0.5%) at pH 7 for 20 minutes by the procedure used in Example 1. The tress was then combed and placed in another aqueous solution containing $NH_4OH$ at 28% (1.2%) and hydrogen peroxide (4%) for an additional 25 minutes. A second tress was colored by a 1-step process for 45 minutes employing an aqueous alcohol (20%) solution containing 3-methyl-4-aminophenol (0.5%), 5-amino-o-cresol (0.5%), $NH_4OH$ at 28% (1.2%) and hydrogen peroxide (4%). Here, all ingredients, precursors, oxidizing agent and base, were first mixed; then the mixture was applied to the hair.

When the two tresses were examined by 8 panelists, it was unanimously agreed that the first tress treated via the 2-step process of the invention acquired a deeper and a more vibrant color compared with the second tress treated by the conventional 1-step process.

These tresses were subsequently shampooed, rinsed, and blown dry with a hair dryer and left overnight at ambient condition. The Tristimulus values before and after shampoo are given in Table 2 below. As in Example 1, these results again indicate that the color developed by the multi-step process of the invention increases the color retention of the dyed hair by about 50%.

TABLE 2

Comparison of shampoo resistance of hair dyed 3-methyl-4-aminophenol, 5-amino-o-cresol by 2-Step and conventional 1-Step process.

| Treatment | Changes in Tristimulus values after shampooing[a] | Changes in Color Index after shampooing |
|---|---|---|
| 2-Step process of this invention | $\Delta L = 1.48$<br>$\Delta a = -1.85$<br>$\Delta b = -0.24$ | $\Delta E = 2.38$ |
| Comparative Example - 1-Step process | $\Delta L = 4.47$<br>$\Delta a = -1.81$<br>$\Delta b = 0.42$ | $\Delta E = 4.84$ |

[a]see footnote in Example 2

Example 4

Illustration of 2-Step Process with Simultaneous Coloring and Conditioning Benefit A 4-gm of Caucasian dark brown hair was treated for 20 minutes in a precursor mixture having the composition shown in Table 3A. The hair was combed to remove excess precursor and subsequently treated for an additional 25 minutes with a developer composition formed by making a 1:1 mixture of the compositions shown in Table 3B and Table 3C. The hair was then rinsed with water and blotted dry with a paper towel. The work (kgf mm) required to comb this tress was measured utiziing an Instron mechanical force tester. A comparative sample was prepared by dyeing a similar tress with a commercial product manufactured by L'Oreal according to the instruction provided in the package. The combing work for this latter tress was also measured. This second tress was further treated with a post-color conditioner included in the package, and the combing work was again measured.

The results are displayed in Table 4 below. It is obvious that the conventional dyeing product increases the surface roughness, and a post conditioner is usually required to reduce this undesired effect. In the present invention, it is possible to include conditioning agents in the development step of a 2-step process to induce color formation and provide conditioning benefit.

TABLE 3A

Composition of Precursor Mixture for Example 4

| | |
|---|---|
| Sodium laureth-2 sulfate (4%) | 50.0 |
| STPP | 0.5 |
| Sodium sulfite | 0.3 |
| Sodium isoascorbate | 0.1 |
| p-aminophenol | 0.1 |
| 5-amino-o-cresol | 0.1 |
| Polyoxyethylene (10) oleyl ether | 1.6 |
| Oleyl alcohol | 1.5 |
| Cetyl alcohol | 0.5 |
| Acrylic polymer emulsion (28%) | 2.0 |
| Water q.s. | to 100.0 |

TABLE 1B

Part 1 of Developer used in Example 4

| | |
|---|---|
| Stearamidopropyl dimethylamine | 0.5 |
| Dicetyldimmonium chloride | 2.1 |
| Stearyl alcohol | 0.2 |
| Ceteareth-20 | 0.3 |
| Cetyl alcohol | 1.8 |
| Polyethylene (20) stearyl ether | 0.7 |

TABLE 1B-continued

| | |
|---|---|
| Dimethicone fluid | 0.1 |
| Cyclopentasiloxane | 1.5 |
| Dimethylaminopropylsiloxane (20%) | 10.0 |
| Ammonium chloride (20%) | 1.8 |
| NH$_4$OH (28%) | 8.0 |
| Water q.s. | to 100.0 |

Part 2 of Developer used in Example 4

| | |
|---|---|
| Citric acid | 0.1 |
| Stearamidopropyl dimethylamine | 0.5 |
| Dicetyldimmonium chloride | 2.1 |
| Stearyl alcohol | 0.4 |
| Ceteareth-20 | 1.1 |
| Cetyl alcohol | 2.3 |
| EDTA | 0.2 |
| Phosphoric acid | 0.1 |
| Acrylic polymer emulsion (28%) | 0.5 |
| Dimethicone fluid | 0.1 |
| Cyclopentasiloxane | 1.8 |
| Hydrogen peroxide (50%) | 16.0 |
| Water q.s. | to 100.0 |

TABLE 4

Combability of 2-Step process combining developer and conditioner in step-2

| Treatment | Combing Work (Kgf mm) |
|---|---|
| Untreated | 3.25 |
| 2-Step process of this invention: Precursor composition of Table 3A Developer/Conditioner 1:1 mixture of part 1 and part 2 of table 3B and 3C | 2.4 |
| Comparative Example: 1-Step Commercial dye ex L'Oreal | 5.75 |
| Comparative Example: 1-Step followed by separate conditioner Commercial dye ex L'Oreal Commercial conditioner ex L'Oreal | 2.0 |

Example 5

Illustration of the Importance of Maintaining the pH in a Region where the Dye Precursors are not in their Anionic Form Piedmont hair (Tress A) was treated for 20 minutes with 3 ml of aqueous solution 10 containing p-phenylenediamine (PPD) (0.21%) and resorcinol (RES) (0.21%), and buffered to pH 10 with ammonium hydroxide (2%). Excess solution on the hair surface was then removed and the tress was emerged in another 3 ml of alkaline solution containing hydrogen peroxide (1%) and ammonium hydroxide (2%), again buffered to pH 10 for an additional 25 minutes. Another 1 gm tress (Tress B) was treated with 3 ml of aqueous pH 7 solution containing the same amount of dye precursors as for Tress A for 20 minutes. Excess solution on the hair surface was removed and the tress was treated with the same amount of peroxide solution as used for Tress A. Both tresses were finally shampooed briefly and rinsed and blown dry with a hair dryer. The two tresses were left in ambient condition overnight before subjected them to the shampoo-fading test.

The pKa of resorcinol is Ca. 9.3. Thus, at pH 10 more than 50% of the resorcinol coupler molecules are in their anionic form while at pH 7 less than 10% of these molecules are in their anionic form and both oxidative dyes are in fact predominantly in their nonionic form at this pH.

The change in Tristimulus values before and after shampoo are given in the Table 3. It is apparent that the tress treated with the precursor solution at pH 7 in the first step retained more color than Tress A which was treated with the precursor solution at pH 10 where more than 50% of the coupler molecules were in the anionic form.

Thus, maintaining the precursors predominantly in their non-anionic forms while they were in contact with the hair before the developer was applied improved the shampoo fade resistance of the treatment by almost a factor of 10 (compare ΔE's for Tress A Vs Tress B).

TABLE 3

| Treatment | Changes in Tristimulus values after shampooing[a] | Changes in Color Index after shampooing |
|---|---|---|
| Tress A Precursors applied at pH 10 and developer applied at pH 10 | Δ L = 0.43 Δ a = 1.11 Δ b = 1.76 | ΔE = 2.13 |
| Tress B - Control Precursors applied at pH 7 and developer applied at pH 10 | Δ L = 0.24 Δ a = −0.16 Δ b = 0.06 | ΔE = 0.295 |

[a]see footnote Example 1

EXAMPLE 6

Illustration of the Improvement in Color Evenness and Depth by Introducing an Optional Alignment and Distributing Step Relative to Simple Blotting Tresses of piedmont hair (5 gm) were treated with an aqueous isopropyl alcohol (10%) solution of p-aminophenol (PAP) (0.3%) and p-amino-cresol (PAOC) (0.35%). The tresses were removed from the treatment solution after 20 minutes, combed to align the hair and to distribute the precursor solution, and immediately placed in another aqueous solution containing hydrogen peroxide (2%) and concentrated ammonium hydroxide (1%) for another 25 minutes. The dyed hair was finally rinsed with water and allowed to dry at ambient temperature. The hair acquired a deep red and even color. In the control experiment, similar tresses were treated by the same procedure described above except the combing step was replaced by towel blotting. The hair color of the control tresses that were simply blotted without an aligning step was judged to be lighter in color and appeared to be more patchy to all 10 panelists who were asked to evaluate the difference between these two sets of hair tresses.

Example 7 this Example Illustrates Formulated Compositions for a 2-Step Process

Composition for the First Step (Application of Dye Precursors):

| INGREDIENTS | WEIGHT % |
|---|---|
| Ceteareth 23 | 3 |
| Cocoamidopropyl betaine | 2 |
| Cetyl alcohol | 2.3 |
| Propylene glycol | 2.5 |
| p-Amino-o-cresol | 2.2 |

-continued

| INGREDIENTS | WEIGHT % |
|---|---|
| Sodium hydroxide | 1.0 |
| p-Phenylenediamine | 1.0 |
| Steareth 3 | 0.8 |
| EDTA | 0.1 |
| p-Aminophenol | 0.5 |
| Isoascrobic acid | 0.1 |
| Sodium bisulfite | 0.2 |
| Fragrance | 0.02 |
| Acetic acid | q.s. pH 7.5 |
| Water | q.s. 100 |

Composition for Second Step:

| INGREDIENTS | WEIGHT % |
|---|---|
| Hydrogen peroxide | 3.0 |
| Cetyl alcohol | 2.0 |
| Ceteareth 23 | 0.5 |
| Phosphoric acid | 1.0 |
| Ammonia (28%) | q.s. pH 10 |
| Water | q.s. 100 |

Example 8

This Example Illustrates a Kit Comprising an Additional Instruction Sheet

The invention also relates to a kit for carrying out the hair coloring method of the invention. The kit may comprise a hair dye precursor part, an optional alignment and distributing means, a color developer comprising a hydrogen peroxide solution and an alkaline pH control solution (e.g., an alkaline buffer solution), and a post treatment solution. Each component may be in a separate container or in a dual container, as described herein. The kit may optionally comprise an integrated system that incorporates two or more of the above means to carry out the above step, e.g., an aligning means and a developer. However, it is preferred to carry out alignment, e.g., combing, is a separate step. The kit also contains written instructions that explain how the compositions of the invention are used. For Example, "Apply dye precursor mixture to hair. After 30 minutes, mix part A and Part B of developer and immediately apply to hair. After 15 minutes rinse hair well and dry".

The consumer can admix the components of the kit according to written instructions, to obtain the aqueous reaction mixture. After treatment for a desired time with the hair dye precursor composition, the implement of the kit is used to align the hair and distribute the dye, followed by application of the developer. The mixture of hair developer and hair dye may be removed, preferably with water or a conventional shampoo or a conventional conditioning shampoo.

Alternatively, and with respect to an embodiment of the invention wherein hair dye precursors are in admixture with the oxidizing compound, there is no need for the consumer to undertake a pre-mixing step, just prior to application to hair. The consumer contacts his or her hair with an admixture of hair dye precursors and the nascent oxidizing compound and waits for about 5 minutes to about 60 minutes to elapse during which time the implement provided with the kit is used to align the hair and distribute the precursor solution. Then the consumer contacts his or her hair with the hair color developer mixture, which in this case comprises an alkaline buffer and allows about 5 minutes to about 60 minutes to elapse, after which the consumer rinses the hair.

A dual package that can be employed in the products and kits of the present invention is disclosed in U.S. Pat. No. 6,082,588 to Markey et al which is hereby incorporated by reference.

A variety of alternative implements can optionally be provided with the kit as described above under aligning means: a simple disposable comb or brush, a sponge or towellete or a combination tool. An example of a combination tool is a comb on whose handle is secured a sponge like absorbent sheet overlapping the teeth of the comb.

Desired change in hair color by the method of the invention is described by the mathematical formula described above. Desired change in hair color can be achieved in a number of other ways. In the first instance, the consumer can initially compare his or her hair color with desired hair color or the hair color of a sample tress. Hair dyeing by the method of the invention can be repeated until his or her hair color matches the desired hair color.

Desired hair color can also be reached by comparing hair after each treatment until it matches hair tresses taken from the consumer during a prior treatment.

Desired hair color can also be reached by testing the hair after each treatment with instruments, which measure the color of the hair. When the measurements of hair color of the treated hair reach a desired level, the treatment hair reach a desired level, the treatment can be stopped.

Indeed, reaching the desired hair color can be achieved by the use of any matching or comparison method commonly employed in the art.

The invention being thus described, it will be obvious that the same may be varied in many ways. Such variations are not to be regarded as a departure from the spirit and scope of the invention and all such modifications are intended to be included within the scope of the following claims.

What is claimed is:

1. A method of providing more vibrant, natural and long-lasting color to hair comprising carrying out the following sequential steps:
    a) contacting the hair with a dye precursor mixture producing a color change, ΔE, of at least about 0.15 units when measured by the In-Vitro Piedmont Color Retention Test, said dye precursor mixture comprising:
        i) a primary intermediate having a pKa in the range from about 3 to about 10 selected from the group consisting of the neutral or salt forms of para-phenylenediamine, derivatized para-phenylenediamines, para-aminophenol, substituted para aminophenols, 4,5-diaminopyrazole, substituted 4,5-diaminopyrazole, polyamino-pyrimidine, hydroxy-polyaminopyrimidine, and other substituted polyaminopyrimidine and mixtures thereof,
        i) an optional coupler having a pKa in the range from about 3 to about 10
    wherein the pH of the precursor solution is selected such that less than 50% of the molecules comprising the primary intermediate and the coupler are in their anionic form when they first contact the hair, and
    b) contacting the hair with a developer mixture capable of inducing oxidation of primary intermediate and coupler in the precursor mixture that is in contact with the hair to form colored species,
wherein the dye precursor mixture remains in contact with the hair for a time period of from about 0.5 to 60 minutes before the hair is contacted with the developer and wherein the primary intermediate and coupler remain substantially inactive during this time period.

2. The method according to claim 1 wherein the primary intermediate and the coupler is each present at a level of from about 0.1 Wt % to about 10 Wt % based on the total weight of the dye precursor mixture and the weight ratio of the primary intermediate to the coupler is in the range of from about 10 to about 0.01.

3. The method according to claim 1 wherein the dye precursor solution contains a nascent oxidizing compound.

4. The method according to claim 1 wherein the dye precursor mixture has a pH selected such that at least 50% of the molecules comprising the primary intermediate and coupler are in their nonionic forms when contacting the hair in step a.

5. The method according to claim 1 further comprising applying to the hair an aligning and distributing means after the hair has been contacted with the dye precursor mixture but before the hair is contacted with the developer mixture.

6. The method according to claim 5 wherein the aligning and distributing means is selected from the group consisting of a comb, a brush, a pick, an elongated element coupled in an open/close relationship, a towelette, a cloth, a sponge and a combination of these implements.

7. The method according to claim 1 wherein the developer comprises an oxidizing agent selected from the group consisting of hydrogen peroxide, urea peroxide, melamine peroxide, sodium perborate, sodium percarbonate and mixtures thereof.

8. The method according to claim 1 wherein the developer mixture comprises an alkaline pH control agent capable of activating the nascent oxidizing agents when present in the precursor mixture to induce oxidation of primary intermediate and coupler in the precursor mixture that is in contact with the hair to form colored species.

9. A kit for providing more vibrant, natural and long-lasting color to hair which comprises:
    a) a dye precursor mixture producing a color change, ΔE, of at least about 0.15 units when measured by the In-Vitro Piedmont Color Retention Test, said dye precursor mixture comprising:
        i) a primary intermediate having a pKa in the range from about 3 to about 10 selected from the group consisting of the neutral or salt forms of para-phenylenediamine, derivatized para-phenylenediamines, para-aminophenol, substituted para aminophenols, 4,5-diaminopyrazole, substituted 4,5-diaminopyrazole, polyamino-pyrimidine, hydroxy-polyaminopyrimidine, and other substituted polyaminopyrimidine and mixtures thereof,
        ii) an optional coupler having a pKa in the range from about 3 to about 10
    wherein the pH of the precursor solution is selected such that less than 50% of the molecules comprising the primary intermediate and the coupler are in their anionic forms when they first contact the hair, and
    b) a developer mixture capable of inducing oxidation of the primary intermediate and coupler to form colored species.

10. The kit according to claim 9 further comprising an aligning and distributing means that contains at least one comb element or at least one brush element.

11. The kit according to claim 9 wherein the dye precursor mixture has a pH selected such that at least 50% of the molecules comprising the primary intermediate and coupler are in their nonionic forms.

12. The kit according to claim 9 further comprising written instructions that direct the user to first apply the dye precursor mixture to the hair, and, without rinsing, to then apply the developer solution to the hair after about 30 seconds to about 60 minutes from the time the dye precursor solution was applied.

13. The kit according to claim 9 further comprising conditioning agents, color sealant, damage control agents, and, hair benefit agents, perfumes, moisturizers and mixtures thereof, either packaged separately or as part of the dye precursor or developer compositions.

14. The kit according to claim 9 wherein the dye precursor mixture contains a nascent oxidizing compound.

* * * * *

UNITED STATES PATENT AND TRADEMARK OFFICE
CERTIFICATE OF CORRECTION

PATENT NO.         : 7,060,111 B2
APPLICATION NO.    : 10/613792
DATED              : May 16, 2006
INVENTOR(S)        : Alexander C. Chan, Padmaja Prem and John Bartolone It is certified that error appears in the above-identified patent and that said Letters Patent is hereby corrected as shown below:

Title page, item 54 and Column 1.
The Title should be replaced by

--METHOD OF PROVIDING MORE VIBRANT, NATURAL AND LONG-LASTING COLOR TO HAIR --

Signed and Sealed this

Fifteenth Day of August, 2006

JON W. DUDAS
*Director of the United States Patent and Trademark Office*

UNITED STATES PATENT AND TRADEMARK OFFICE
CERTIFICATE OF CORRECTION

| | | |
|---|---|---|
| PATENT NO. | : 7,060,111 B2 | Page 1 of 1 |
| APPLICATION NO. | : 10/613792 | |
| DATED | : June 13, 2006 | |
| INVENTOR(S) | : Alexander C. Chan, Padmaja Prem and John Bartolone | |

It is certified that error appears in the above-identified patent and that said Letters Patent is hereby corrected as shown below:

Title page, item 54 and Column 1.
The Title should be replaced by

--METHOD OF PROVIDING MORE VIBRANT, NATURAL AND LONG-LASTING COLOR TO HAIR--

This certificate supersedes Certificate of Correction issued August 15, 2006.

Signed and Sealed this

Nineteenth Day of September, 2006

JON W. DUDAS
*Director of the United States Patent and Trademark Office*